US010863948B2

(12) United States Patent
An et al.

(10) Patent No.: US 10,863,948 B2
(45) Date of Patent: Dec. 15, 2020

(54) HEART FAILURE STRATIFICATION BASED ON RESPIRATORY PATTERN

(71) Applicant: Cardiac Pacemakers, Inc., St. Paul, MN (US)

(72) Inventors: Qi An, Blaine, MN (US); Jianjun Yuan, Minneapolis, MN (US); Pramodsingh Hirasingh Thakur, Woodbury, MN (US); Yi Zhang, Plymouth, MN (US); Rezwan Ahmed, Arden Hills, MN (US); Viktoria A. Averina, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 120 days.

(21) Appl. No.: 16/182,353

(22) Filed: Nov. 6, 2018

(65) Prior Publication Data
US 2019/0167205 A1 Jun. 6, 2019

Related U.S. Application Data

(60) Provisional application No. 62/595,506, filed on Dec. 6, 2017.

(51) Int. Cl.
*A61B 5/00* (2006.01)
*A61B 5/0205* (2006.01)
(Continued)

(52) U.S. Cl.
CPC .......... *A61B 5/7275* (2013.01); *A61B 5/0205* (2013.01); *A61B 5/0809* (2013.01);
(Continued)

(58) Field of Classification Search
CPC ... A61B 5/0205; A61B 5/0538; A61B 5/0809; A61B 5/0816; A61B 5/091;
(Continued)

(56) References Cited

U.S. PATENT DOCUMENTS 7,678,061 B2   3/2010   Lee et al.
7,775,983 B2   8/2010   Zhang et al.
(Continued)

OTHER PUBLICATIONS

Verceles, Avelino C., et al., "Testing the prognostic value of the rapid shallow breathing index in predicting successful weaning in patients requiring prolonged mechanical ventilation", Heart Lung. 2012 ; 41(6): 546-552.

*Primary Examiner* — George Manuel
(74) *Attorney, Agent, or Firm* — Schwegman Lundberg & Woessner, P.A.

(57) ABSTRACT

Systems and methods for monitoring patients for risk of worsening heart failure (WHF) are discussed. A patient management system includes a receiver to receive patient respiration measurement. A respiratory pattern analyzer circuit measures respiratory pattern indicative of rapid-shallow breathing pattern from the received respiration measurement, and determine a respiratory pattern variability indicator. A risk analyzer circuit determines patient WHF risk using the respiratory pattern variability indicator. The system may use the WHF risk to guide WHF event detection, or to deliver or adjust a heart failure therapy.

20 Claims, 6 Drawing Sheets

(51) Int. Cl.
 *A61B 5/08* (2006.01)
 *A61B 7/04* (2006.01)
 *G16H 50/30* (2018.01)
 *A61B 5/091* (2006.01)

(52) U.S. Cl.
 CPC .......... *A61B 5/0816* (2013.01); *A61B 5/4836* (2013.01); *A61B 5/686* (2013.01); *A61B 7/04* (2013.01); *G16H 50/30* (2018.01); *A61B 5/0538* (2013.01); *A61B 5/091* (2013.01)

(58) Field of Classification Search
 CPC ..... A61B 5/4836; A61B 5/686; A61B 5/7275; A61B 7/04; G16H 20/40; G16H 40/63; G16H 50/30
 See application file for complete search history.

(56) References Cited

U.S. PATENT DOCUMENTS

| | | | |
|---|---|---|---|
| 2010/0026479 A1* | 2/2010 | Tran | A61B 5/02042 340/501 |
| 2012/0132211 A1* | 5/2012 | Halperin | A61B 5/1116 128/207.14 |
| 2014/0031643 A1 | 1/2014 | An et al. | |
| 2015/0038854 A1 | 2/2015 | Zhang et al. | |

\* cited by examiner

HEART FAILURE STRATIFICATION BASED ON RESPIRATORY PATTERN

CLAIM OF PRIORITY

This application claims the benefit of priority under 35 U.S.C. § 119(e) of U.S. Provisional Patent Application Ser. No. 62/595,506, filed on Dec. 6, 2017, which is herein incorporated by reference in its entirety.

TECHNICAL FIELD

This document relates generally to medical devices, and more particularly, to systems, devices and methods for assessing a patient risk of worsening heart failure using respiration pattern variability.

BACKGROUND

Congestive heart failure (CHF) is a leading cause of death in the United States and globally. CHF refers to loss of pumping power of the heart, resulting in the inability to deliver enough blood to meet the demands of peripheral tissue. CHF patients typically have enlarged heart with weakened cardiac muscles, resulting in reduced contractility and poor cardiac output of blood. CHF may be treated by drug therapy, or by an implantable medical device (IMD) such as for providing electrostimulation therapy. CHF is usually a chronic condition, but can occur suddenly. It can affect the left heart, right heart or both sides of the heart.

Dyspnea, generally refers to a sensation of shortness of breath or difficult breathing, is a common symptom of CHF. Dyspnea may be caused by heart or lung disorders, strenuous activity, high anxiety or stress. Dyspnea derives from interactions among multiple physiological, psychological, social, and environmental factors, and may induce secondary physiological and behavioral responses. Dyspnea may be classified as chronic, acute, or terminal. Chronic dyspnea has a variable intensity and persistent shortness of breath. This is most often seen in patients with chronic obstructive pulmonary disease (COPD). Acute dyspnea causes episodes of shortness of breath with high intensity.

Some IMDs can monitor CHF patients and detect events leading to worsening heart failure (WHF). These IMDs may include or be coupled to sensors to sense physiologic signals from a patient. Frequent patient monitoring may help reduce heart failure hospitalization. Identification of patient at an elevated risk of developing WHF, such as heart failure decompensation, may help ensure timely treatment and improve prognosis and patient outcome. Identifying and safely managing the patients at elevated risk of WHF can avoid unnecessary medical interventions, hospitalization, and thereby reduce healthcare cost.

An IMD may contain electronic circuitry, such as a pulse generator, that can generate and deliver electrostimulation to excitable tissue or organs, such as a heart. The electrostimulation may help restore or improve a CHF patient's cardiac performance, or rectify cardiac arrhythmias. One example of the electrostimulation therapy is resynchronization therapy (CRT) for correcting cardiac dyssynchrony in CHF patients.

SUMMARY

Various types of disordered respiration may be associated with CHF. Respiration rate is linked to the patient's physical condition and is indicative of the patient's disease or health state. In some types of chronic diseases, changes in respiratory rate are gradual over time and may be measured over months or years. However, in heart failure decompensation, increases in respiratory rate can occur over days or weeks. Clinical data collected in the ambulatory setting has demonstrated a statistically significant difference between respiration rate distributions from healthy subjects when compared to patients with CHF.

Rapid-shallow breathing (RSB) is a typical pattern associated with dyspnea caused by heart or lung disorders, strenuous activity, high anxiety or stress. RSB is different from tachypnea (rapid breathing) and hyperpnea (deep breathing). Tachypnea and hyperpnea can occur with hyperventilation, or over breathing beyond what is required to maintain arterial blood gases within normal limits, whereas hyperpnea may be an appropriate increase in breathing such as with exercise. RSB can be associated with symptoms of shortness of breath, or dyspnea. Dyspnea derives from interactions among multiple physiological, psychological, social, and environmental factors, and may induce secondary physiological and behavioral responses. Fear or anxiety may create even more distress in dyspneic patients.

CHF patients frequently present with dyspnea with exertion, orthopnea (a sensation of breathlessness in a recumbent position), or paroxysmal nocturnal dyspnea (a sensation of shortness of breath that awakens the patient). Dyspnea may occur initially upon exertion, but in advanced CHF it may occur at rest, or when lying down. In diastolic heart failure, increased pressure can build up in the heart during the period of relaxation, or diastole.

Although dyspnea may be related to abnormal pulmonary fluid accumulation in CHF patients, dyspnea may have causes other than CHF. For example, acute dyspnea or respiratory distress may be caused by asthma, cardiac tamponade, hypotension, pulmonary embolism, pneumonia, or upper airway obstruction, among others. Chronic dyspnea can also indicate chronic conditions other than CHF, such as asthma, chronic obstructive pulmonary disease (COPD), deconditioning, or non-cardiac or non-pulmonary causes such as metabolic conditions, pain, neuromuscular disorders, panic disorders and anxiety, or hyperventilation, among others. Therefore, although dyspnea symptom is a useful diagnostic of WHF, it can be non-specific in some patients. Similarly, respiratory measurements, such as respiratory rate or RSB, may not be very specific to WHF in some patients. For example, patients with chronic respiratory disease, such as asthma and COPD, may present symptoms including chronic coughing, wheezing, shortness of breath, or hyper-responsiveness to airflow during inspiration, among others. Particularly in an ambulatory setting, respiration measurement may be susceptible to physiological or environmental interferences or be contaminated by noise. The confounding diseases or conditions, or the noise and interferences, may adversely affect the accuracy and reliability of WHF event detection or WHF risk stratification.

The present inventors have recognized a challenge in heart failure monitoring, namely an accurate and reliable identification of patients at elevated risks of WHF. The present inventors have also recognized that changes in respiratory pattern, such as an increase in respiratory rate variability or a variability of rapid-shallow breathing index (RSBI), may improve sensitivity, specificity, and predictive value of WHF event detection or WHF risk stratification. As a result, better patient management and reduction in healthcare cost may be achieved.

This document discusses, among other things, a patient management system for assessing patient risk of WHF based on respiratory pattern variability. The system may receive respiratory measurement such as a respiratory rate, tidal volume, respiration timing, or respiration depth. A respiratory pattern analyzer circuit may measure a respiratory pattern indicative of RSB pattern. The respiratory pattern analyzer circuit may determine a respiratory pattern variability indicator representative of a temporal variation of the measured respiratory pattern. A risk analyzer circuit may generate a WHF risk indicator using the respiratory pattern variability. The system may use the WHF risk to guide WHF event detection, or to deliver or adjust a heart failure therapy.

Example 1 is a system for assessing a patient risk for a future worsening heart failure (WHF) event. The system comprises a signal receiver circuit to receive a respiratory signal from the patient, a processor circuit, and a risk analyzer circuit. The processor circuit may include a respiratory pattern analyzer circuit to measure a respiratory pattern using the received respiratory signal and to determine a respiratory pattern variability indicator indicative of temporal variation of the measured respiratory pattern. The risk analyzer circuit may generate a WHF risk indicator using the determined respiratory pattern variability indicator.

In Example 2, the subject matter of Example 1 optionally includes the respiratory pattern that may include a rapid-shallow breathing index (RSBI), and the respiratory pattern variability indicator may include an RSBI variability. The risk analyzer circuit may generate the WHF risk indicator using the RSBI In Example 3, the subject matter of Example 2 optionally includes a sensor circuit coupled to an impedance sensor that may sense a thoracic impedance correlated to respiration. The respiratory patter analyzer circuit may be configured to detect a respiratory rate and a tidal volume using the sensed thoracic impedance, and to generate the RSBI based on a ratio of the detected respiratory rate to the detected tidal volume.

In Example 4, the subject matter of any one or more of Examples 2-3 optionally includes the respiratory pattern analyzer circuit that may determine the RSBI variability using measurements of daily representative RSBI over multiple days.

In Example 5, the subject matter of Example 4 optionally includes the respiratory pattern analyzer circuit that may further configured to determine a baseline RSBI using the measurements of daily representative RSBI over multiple days. The risk analyzer circuit may be configured to generate the WHF risk indicator further using the baseline RSBI.

In Example 6, the subject matter of any one or more of Examples 4-5 optionally includes the daily representative RSBI that may include a daily minimum RSBI.

In Example 7, the subject matter of any one or more of Examples 4-5 optionally includes the daily representative RSBI that may include a specific percentile of daily RSBI measurements, the specific percentile being lower than 50-th percentile.

In Example 8, the subject matter of any one or more of Examples 1-7 optionally includes an activity detection circuit to detect patient physical activity. The signal receiver circuit may be configured to receive a respiratory signal when the detected patient physical activity satisfies a specific condition.

In Example 9, the subject matter of any one or more of Examples 2-7 optionally includes the signal receiver circuit to receive a heart sounds signal. The processor circuit may include a heart sound analyzer circuit that may generate a heart sound metric using the received heart sounds signal. The risk analyzer circuit may be configured to: generate the WHF risk indicator using the RSBI variability if the received heart sounds signal fails to satisfy a signal quality condition; and generate the WHF risk indicator using the heart sound metric if the received heart sounds signal satisfies the signal quality condition.

In Example 10, the subject matter of any one or more of Examples 1-9 optionally includes the respiratory pattern analyzer circuit that may generate, from the sensed respiratory signal, one or more respiratory metrics including a respiratory rate trend, a respiratory rate variability over time, a tidal volume trend, or a tidal volume variability over time. The risk analyzer circuit may be configured to generate the VHF risk indicator further using the generated one or more respiratory metrics.

In Example 11, the subject matter of Example 10 optionally includes the generated one or more respiratory metrics that may include a respiratory rate variability. The risk analyzer circuit may be configured to generate the WHF risk indicator using the RSBI variability and the respiratory rate variability.

In Example 12, the subject matter of any one or more of Examples 10-11 optionally includes the respiratory pattern analyzer circuit that may generate a tidal volume trend and a respiratory rate trend from the sensed respiratory signal. The risk analyzer circuit may be configured to: generate the WHF risk indicator using the RSBI variability if the tidal volume trend satisfies a quality condition; and generate the WHF risk indicator using the respiratory rate trend if the tidal volume trend fails to satisfy the quality condition.

In Example 13, the subject matter of any one or more of Examples 1-12 optionally includes n output circuit that may output the WHF risk indicator to a user or a process.

In Example 14, the subject matter of any one or more of Examples 1-13 optionally includes a detector circuit that may detect a WHF event based on the generated VHF risk indicator.

In Example 15, the subject matter of any one or more of Examples 1-14 optionally includes a therapy circuit that may generate a heart failure therapy when the WHF risk indicator satisfies a specific condition.

Example 16 is a method for assessing a patient risk for a future worsening heart failure (WHF) event using a medical system. The method comprises steps of: receiving a respiratory signal from the patient via a signal receiver circuit; measuring, via a respiratory pattern analyzer circuit, a respiratory pattern from the received respiratory signal; determining a respiratory pattern variability indicator indicative of temporal variation of the measured respiratory pattern; and generating a WHF risk indicator using the determined respiratory pattern variability indicator via a risk analyzer circuit.

In Example 17, the subject matter of Example 16 optionally includes the respiratory pattern that may include a rapid-shallow breathing index (RSBI), the respiratory pattern variability indicator that may include an RSBI variability. The WHF risk indicator may be generated based on at least the RSBI variability.

In Example 18, the subject matter of Example 17 optionally includes the RSBI variability determined using measurements of daily representative RSBI over multiple days.

In Example 19, the subject matter of Example 18 optionally includes determining a baseline RSBI using the measurements of daily representative RSBI over multiple days. The WHF risk indicator may be generated further based on the baseline RSBI.

In Example 20, the subject matter of Example 17 optionally includes generating a heart sound metric using a heart sounds signal. The generation of the WHF risk indicator may include steps of: generating the WHF risk indicator using the RSBI variability if the received heart sounds signal satisfies a signal quality condition; and generating the WHF risk indicator using the heart sound metric if the received heart sounds signal fails to satisfy the signal quality condition.

In Example 21, the subject matter of Example 16 optionally includes generating one or more respiratory metrics from the sensed respiratory signal. The one or more respiratory metrics may include a respiratory rate trend, a respiratory rate variability over time, a tidal volume trend, or a tidal volume variability over time. The WHF risk indicator may be generated further based on the one or more respiratory metrics.

In Example 22, the subject matter of Example 21 optionally includes the one or more respiratory metrics that may include a tidal volume trend and a respiratory rate trend from the sensed respiratory signal. The generation of the WHF risk indicator may include steps of: generating the WHF risk indicator using the RSBI variability if the tidal volume trend satisfies a quality condition; and generating the WHF risk indicator using the respiratory rate trend if the tidal volume trend fails to satisfy the quality condition.

In Example 23, the subject matter of Example 16 optionally includes delivering a heart failure therapy when the WHF risk indicator satisfies a specific condition.

Various embodiments described herein can improve the medical technology of device-based heart failure patient management, particularly computerized WHF risk assessment. As discussed above, dyspnea may present in various cardiac, pulmonary, neurological, or psychological disorders. Conventional sensor-based respiration detection faces a challenge of reduced specificity to WHF. The present inventors have recognized that respiratory pattern variability, such as RSB pattern variability, has a predictive power complementary to that of respiratory rate or other respiratory parameters. Systems and methods that utilize the respiratory pattern variability as discussed in this document may enhance the accuracy (e.g., by reducing false positive rate of prediction of high WHF risk) of WHF risk stratification, while at little to no additional cost. An improvement in heart failure patient management can reduce hospitalization and healthcare costs associated with patient management.

Additionally, as the respiratory pattern variability is clinically more relevant to patient WHF risk, acquiring and storing the respiratory pattern variability allows for more efficient device memory usage. With more accurate WHF risk assessment, fewer false positive WHF events may be detected, and fewer therapy interventions may be required. Accordingly, device battery life can be extended, and fewer unnecessary drugs and procedures may be scheduled, prescribed, or provided. As such, overall system cost savings may be realized.

Although systems and methods are described as being operated or exercised by clinicians, the entire discussion herein applies equally to organizations, including hospitals, clinics, and laboratories, and other individuals or interests, such as researchers, scientists, universities, and governmental agencies, seeking access to the patient data.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring a patient for WHF. A patient management system includes a receiver to receive patient respiration measurement. A respiratory pattern analyzer circuit may measure a respiratory pattern indicative of rapid-shallow breathing (RSB) pattern from the received respiration measurement, and determine a respiratory pattern variability indicator of the respiratory pattern. A risk analyzer circuit may determine patient WHF risk using the respiratory pattern variability indicator. A therapy circuit may deliver or adjust a heart failure therapy based on the WHF risk indicator.

Figure 1:
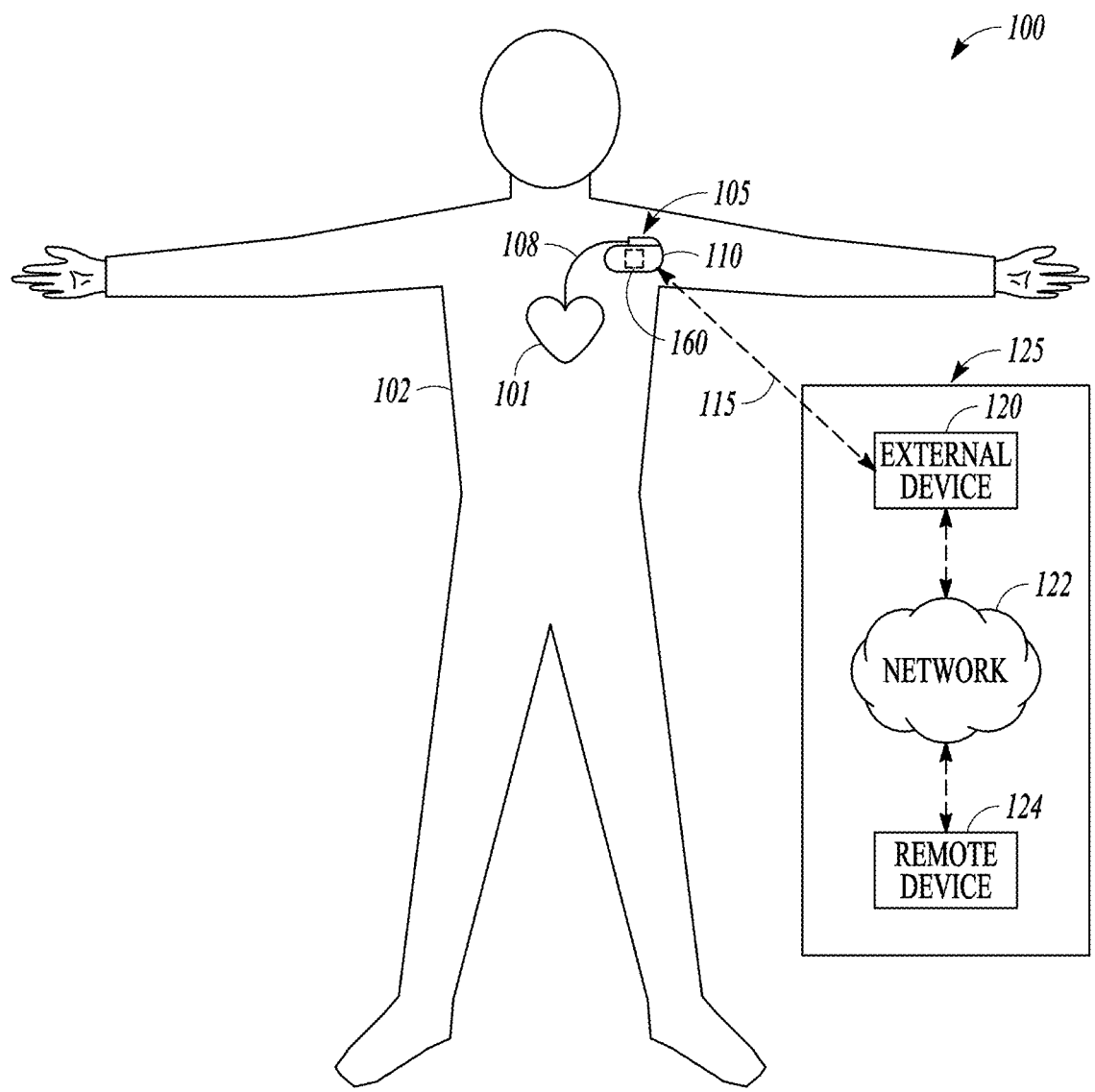
FIG. 1 illustrates generally an example of a patient monitor system and portions of an environment in which the system may operate.

FIG. 1 illustrates generally an example of a patient monitor system 100 and portions of an environment in which the system 100 may operate. The patient monitor system 100 may chronically monitor a patient 102 to assess patient risk of developing WHF. Portions of the system 100 may be ambulatory. Portions of the system 100 may be disposed in a patient home or office, a hospital, a clinic, or a physician's office.

As illustrated in FIG. 1, the patient monitor system 100 may include an ambulatory system 105 associated with the patient 102, an external system 125, and a telemetry link 115 providing for communication between the ambulatory system 105 and the external system 125. The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart wearables, or smart accessories.

By way of example and not limitation, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may include a hermetically sealed can that houses one or more of a sensing circuit, a control circuit, a communication circuit, and a battery, among other components. The sensing circuit may sense a physiologic signal, such as by using a physiologic sensor or the electrodes associated with the lead system 108. The physiologic signals may contain information about patient physiologic response to a precipitating event associated with onset of a future WHF event. The physiologic signal may represent changes in patient hemodynamic status. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiratory rate, tidal volume, respiratory sounds, body weight, or body temperature.

The AMD 110 may include a risk assessment circuit 160 configured to assess a patient risk of developing a worsened chronic disease or condition, such as WHF. The risk assessment circuit 160 may include a sensor circuit to receive respiration measurements such as respiratory rate, depth, timing, regularity, or respiratory pattern. The risk assessment circuit 160 may trend the respiration measurements over time, determine respiratory pattern variability, and generate a WHF risk indicator using at least the respiratory pattern variability. The WHF risk indicator indicates the patient's risk of developing a future WHF event, such as a heart failure decompensation event. Examples of the WHF risk assessment are described below, such as with reference to FIGS. 2-6B. In various examples, the risk assessment circuit 160 may also be configured to detect worsening of other diseases or conditions including, for example, cardiac arrhythmias, syncope, respiratory disease such as COPE or asthma, or renal dysfunctions, among other medical conditions.

The AMD 110 may include a therapy unit that may generate and deliver a therapy to the patient. The therapy may be preventive (e.g., to prevent development into a full-blown condition, decompensation, etc.), or therapeutic (e.g., to treat heart failure or alleviate complications) in nature, and may modify, restore, or improve patient physiologic functionalities. Examples of the therapy may include electrical, magnetic, or other forms of therapy. In some examples, the AMD 110 may include a drug delivery system such as a drug infusion pump device to deliver drug therapy to the patient. In some examples, the AMD 110 may monitor patient physiologic responses to the delivered to assess the efficacy of the therapy.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to generate a WHF risk indicator, or optionally delivering or adjusting a therapy to the patient 102. The external system 125 may communicate with the AMD 110 via the communication lit 115. The device data received by the external system 125 may include real-time or stored physiologic data from the patient 102, diagnostic data, responses to therapies delivered to the patient 102, or device operational status of the AMD 110 (e.g., battery status and lead impedance). The communication link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device. The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

The remote device 124 may include a centralized server acting as a central hub for collected patient data storage and analysis. The patient data may include data collected by the AMD 110, and other data acquisition sensors or devices associated with the patient 102. The server may be configured as a uni-, multi- or distributed computing and processing system. In an example, the remote device 124 may include a data processor configured to perform heart failure detection or risk stratification using respiration data received by the AMD 110. Computationally intensive algorithms, such as machine-learning algorithms, may be implemented in the remote device 124 to process the data retrospectively to detect WHF or analyze patient WHF risk. The remote device 124 may generate an alert notification. The alert notifications may include a Web page update, phone or pager call, E-mail, SMS, text or "Instant" message, as well as a message to the patient and a simultaneous direct notification to emergency services and to the clinician. Other alert notifications are possible.

One or more of the external device 120 or the remote device 124 may output the WHF detection or the WHF risk to a system user such as the patient or a clinician. The external device 120 or the remote device 124 may include respective display for displaying the physiologic data acquired by the AMD 110. The physiologic data may be presented in a table, a chart, a diagram, or any other types of textual, tabular, or graphical presentation formats. The external device 120 or the remote device 124 may include a printer for printing hard copies of signals and information related to the generation of WHF risk indicator. The presentation of the output information may include audio or other media formats. In an example, the output unit 254 may generate alerts, alarms, emergency calls, or other forms of warnings to signal the system user about the WHF detection or WHF risk. The clinician may review, perform further analysis, or adjudicate the WHF detection or WHF risk. The WHF detection or the WHF risk, optionally along with the data acquired by the AMD 110 and other data acquisition sensors or devices, may be output to a process such as an instance of a computer program executable in a microprocessor. In an example, the process may include an automated generation of recommendations for initiating or adjusting a therapy, or a recommendation for further diagnostic test or treatment.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
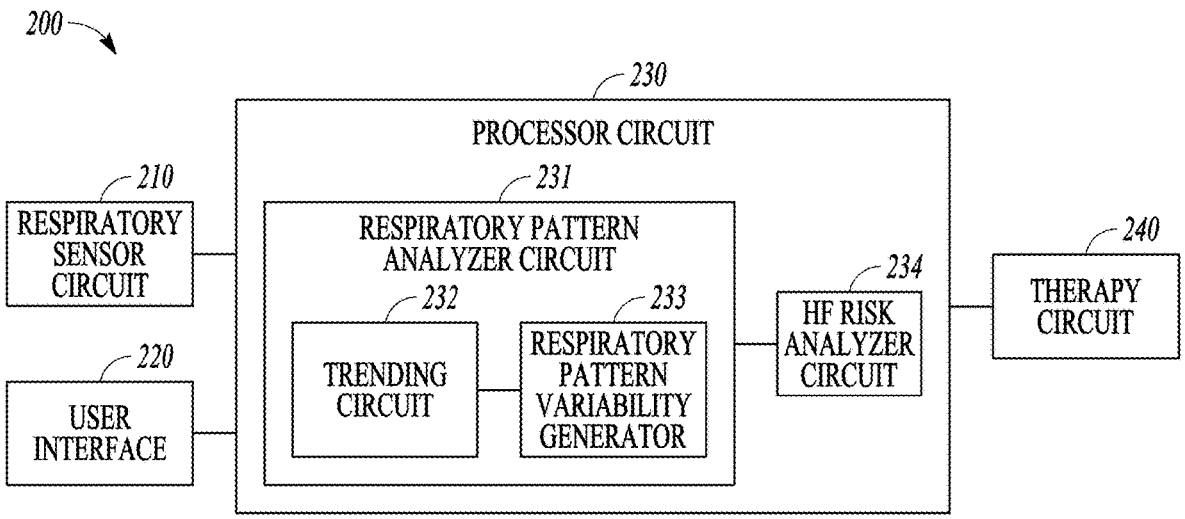
FIG. 2 illustrates generally an example of a heart failure monitor system to assess patient risk of WHF.

FIG. 2 illustrates generally an example of a heart failure monitor system 200 to assess a risk of WHF of a patient. At least a portion of the heart failure monitor system 200 may be implemented in the AMD 110, the external system 125 such as one or more of the external device 120 or the remote device 124, or distributed between the AMD 110 and the external system 125. The heart failure monitor system 200 may include one or more of a respiratory sensor circuit 210, a user interface 220, and a processor circuit 230 for processing respiratory information to generate an indication of WHF, and an optional therapy circuit 240 for delivering a heart failure therapy.

The respiratory sensor circuit 210 may include a sense amplifier circuit to sense at least one physiologic signal from a patient. The respiratory sensor circuit 210 may be coupled to an implantable, wearable, or otherwise ambulatory sensor or electrodes associated with the patient. The sensor may be incorporated into, or otherwise associated with an ambulatory device such as the AMD 110. Examples of the physiologic signals for detecting the precipitating event may include surface electrocardiography (ECG) sensed from electrodes placed on the body surface, subcutaneous ECG sensed from electrodes placed under the skin, intracardiac electrogram (EGM) sensed from the one or more electrodes on the lead system 108, heart rate signal, physical activity signal, or posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiologic response to activity, apnea hypopnea index, one or more respiratory signals such as a respiratory rate signal or a tidal volume signal, brain natriuretic peptide (BNP), blood panel, sodium and potassium levels, glucose level and other biomarkers and bio-chemical markers, among others. In some examples, the physiologic signals sensed from a patient may be stored in a storage device, such as an electronic medical record system, and the respiratory sensor circuit 210 may be configured to receive a stored physiologic signal from the storage device in response to a user input or triggered by a specific event.

In various examples, the respiratory sensor circuit 210 may be coupled to an implantable, wearable, holdable, or other ambulatory respiratory sensors configured to acquire a respiratory signal. Various respiratory sensors may be used to measure directly or indirectly a change in airflow or a change in lung volume during respiratory cycles. In an example, a flowmeter may be configured to sense directly the airflow in the respiratory system or volume change in the lungs. In another example, the respiratory sensor may be coupled to electrodes attached to or implanted in the patient to sense the respiratory signal from the patient. Some respiratory sensors may sense a physiologic signal modulated by respiration. In an example, the thoracic impedance may vary at different respiratory phases, such that the impedance increases during inspiration and decreases during expiration. The thoracic impedance may be measured using electrodes on an implantable lead coupled to an implantable medical device. In an example, thoracic impedance may be measured between an electrode on a right ventricular and the can housing of the implantable device implanted at a pectoral region, between an electrode on a left ventricle and the can housing of the implantable device, or between a right atrium electrode and the can housing of the implantable device. The thoracic impedance may alternatively be measured using non-invasive surface electrodes removably attached to a patient chest.

In various examples, respiration may be sensed using one or more of a strain sensor configured to sense changes in chest muscle tension corresponding to respiration cycles, an accelerometer to measure acceleration associated with displacement or movement of chest walls corresponding to respiration, or an acoustic sensor to sense cardiac acoustic signal that is modulated by respiration. In an example, respiratory signal may be extracted from a cardiac electrical signal modulated by respiratory signal, such as a ECG signal. During inspiration, the diaphragm shift downwards away from the apex of the heart. The increased filling of the lungs further stretches the apex of the heart towards the abdomen. During expiration, the lung volume reduces, and the diaphragm elevates upwards toward the heart, which compresses the apex of the heart towards the breast. As a result, the angle of the electric cardiac vector that gives rise to the ECG signal changes during inspiration and respiratory phases, which leads to cyclic variation in R-wave amplitude on the ECG signal. The respiratory signal can be obtained from the R-wave amplitude signal using demodulation method, such as by filtering an R-wave amplitude trend through a low-pass filter or a bandpass filter. Other respiratory sensors may alternatively include patient-external respiratory bands, respiration flowmeter, implantable or patient-external breath sound detector, blood oxygen detector, and other sensors configured to sense a respiration-modulated physiologic signal, which can be found in Lee et al., U.S. Pat. No. 7,678,061 entitled "System and method for characterizing patient respiration", filed on Apr. 15, 2004, which is incorporated herein by reference in its entirety.

The respiratory sensor circuit 210 may include one or more sub-circuits to digitize, filter, or perform other signal conditioning operations on the sensed physiologic signal. The respiratory sensor circuit 210 may detect from the sensed respiratory signal a plurality of respiratory cycles, and determine for each respiratory cycle a respiratory cycle period, or a respiratory rate. The respiratory sensor circuit 210 may detect, within each respiratory cycle, an inspiration phase and an expiration phase. The inspiration phase is a period between an end-of-expiration state and the next end-of-inspiration state. The expiration phase is a period between an end-of-inspiration state and the next end-of-expiration state. In an example where the respiratory sensor directly or indirectly measures the lung volume, the end-of-expiration state may correspond to the minimal lung volume within a specified detection window; and the end-of-inspiration state may correspond to the maximal lung volume with a specified detection window. In another example where the respiratory sensor senses thoracic impedance, the thoracic impedance increases when the air volume in the lungs increases. The end-of-expiration state may correspond to the minimal thoracic impedance within a specified detection window; and the end-of-inspiration state may correspond to the maximal thoracic impedance within a specified detection window. In another example, the respiratory sensor may sense acceleration of chest movements associated with respiration.

The user interface 220 may include a display screen and a user input device. The input device may include a keyboard, an on-screen keyboard, a mouse, a trackball, a touchpad, a touch-screen, or other pointing or navigating devices. A user, such as the patient or a clinician, may use the input device to enter information about patient information such as patient demographics, medical history, dyspnea symptoms, or other medical information. A user may program one or more parameters for system components, such as the respiratory sensor circuit 210, the respiratory pattern analyzer circuit 231, the heart failure risk analyzer circuit 234, or the therapy circuit 240. The display screen may be configured to display sensed respiratory signal and user provided patient information.

The processor circuit 230 may generate a WHF risk indicator using the sensed respiratory signal. The processor circuit 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The respiratory pattern analyzer circuit 231 may include circuit sets comprising one or more other circuits or sub-circuits, including a respiratory pattern analyzer circuit 231 and a heart failure risk analyzer circuit 234. These circuits or sub-circuits may, either individually or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The respiratory pattern analyzer circuit 231 may include a trending circuit 232 and a respiratory pattern variability generator 233. The trending circuit 232 may trend one or more respiratory metrics generated from the respiratory signal over time. Examples of the respiratory metrics may include a respiratory rate, a tidal volume, a minute ventilation, a respiratory sound, or a respiratory pattern, among other respiratory metrics. In an example, the respiratory pattern may include a rapid-shallow breathing index (RSBI) computed as a ratio of a respiratory rate measurement to a tidal volume measurement. Other examples of respiratory pattern may include Cheyne-Stokes pattern, cluster breathing, Kussmaul's breathing, apneustic breathing, or ataxic breathing. In an example, the trending circuit 232 may generate one or more of a respiratory rate trend (RRT), a tidal volume trend, a minute ventilation trend, or an RSBI trend, among other respiratory metric trends.

The respiratory pattern variability generator 233 may generate a variability indicator of a trended respiratory metric. Generation of the respiratory variability indicator may be continuous, periodical at specified frequency (e.g., every 3-5 days), or triggered by a user command or specified event such as a detention of a change in patient medical condition. In an example, the variability indicator includes a respiratory pattern variability indicator, such as an RSBI variability, indicative of temporal variation of a respiratory pattern. Examples of variability may include a standard deviation, a variance, a range (e.g., a difference between minimum and maximum, an interquartile range between upper and lower quartiles, a difference between $10^{th}$ to $90^{th}$ percentiles or other ranges), or other measures of spreadness of the respiratory metric. The variability may be computed within a specified time period, such as a minute, a day, several days, or other specified time range. In an example, the RSBI variability may be computed using measurements of daily representative RSBI over a number of days. In an example, the daily representative RSBI aggregates data from a subset of a 24-hour window. In various examples, the daily representative RSBI may include a daily minimum RSBI, a daily maximum RSBI, a daily median RSBI, a daily mean RSBI, or specific percentile of multiple RSBI measurements during a day (denoted by $RSBI_{X\%}$). In an example, the specific percentile may be lower than 50-th percentile. For example, a daily 25-th percentile of RSBI ($RSBI_{25\%}$) represents an RSBI value such that 25% of a plurality of RSBI measurements made on one day are less than or equal to $RSBI_{25\%}$. When a subject is physically active, both respiratory rate and tidal volume may increase to meet the increased metabolic demands, and tidal volume usually increases faster or by a larger relative amount that respiratory rate. This may result in a decrease in RSBI at higher physical activity level. As such, a lower percentile (e.g., <50%) RSBI represents rapid-shallow breathing pattern at elevated physical activities. Because heart failure patients are more likely to demonstrate shortness of breath when they are active, a lower percentile RSBI may be a better predictor to patient heart failure status than a higher percentile (e.g., >50%) RSBI. In an example, daily $RSBI_{X\%}$ may be measured consecutively for 5-7 days, and a variability may be determined using the daily $RSBI_{25\%}$ over the 5-7 days.

The heart failure risk analyzer circuit 234, coupled to the respiratory pattern analyzer circuit 231, may be configured to generate a WHF risk indicator using at least the respiratory pattern variability indicator. The present inventors have recognized that the variability of respiratory pattern has a predictive power complementary to that of the other respiratory metrics. For example, the variability of RSBI is found to be less correlated to the variability of respiratory rate. Incorporating the RSBI variability into a risk stratification system may enhance the accuracy and reliability of a prediction of patient WHF risk. Examples of performance of WHF risk stratification based on RSBI variability alone or together with other respiratory metrics are discussed below, such as with reference to FIG. 6.

The heart failure risk analyzer circuit 234 may compare the respiratory pattern variability indicator (e.g., the RSBI variability) to one more threshold values or one or more value ranges, and classify the patient WHF risk into a risk category. In some examples, the respiratory pattern variability generator 233 may generate higher-order (higher than the second-order) statistics of one or more of the respiratory metrics. The heart failure risk analyzer circuit 234 may determine the WHF risk indicator using two or more respiratory metric trends, and/or variability or higher-order statistics of the respiratory metrics.

In an example, the heart failure risk analyzer circuit 234 may generate the WHF risk indicator (R) using a pre-determined mapping f of a plurality of respiratory parameter trends $(X_1, X_2, \ldots, X_K)$, that is, $R=f(X_1, X_2, \ldots, X_K)$, where K denotes the number of respiratory metrics. In an example, the mapping f may be represented by a look-up table or an association map, where each pre-determined WHF risks, R(i), is associated with the K respiratory metrics falling within respective value ranges, denoted by $X_1(i)$, $X_2(i), \ldots, X_K(i)$. In an example, the respiratory parameter trends include respiratory rate trend, a respiratory rate variability, an RSBI trend, an RSBI variability, a tidal volume trend, or a tidal volume variability, among others. In an example, a WHF risk category may be characterized by respiratory rate between 15-25 breaths per minute, and respiratory rate variability (e.g., represented by maximum variation within a minute, a day, or other specified time range, $10^{th}$ to $90^{th}$ percentile range within a day, or a standard deviation within a day) between 0-6 bpm.

Additionally or alternatively, the heart failure risk analyzer circuit 234 may determine the WHF risk indicator using a weighted combination of the respiratory variability indicators and other respiratory metrics. The weight factors may be determined based on performance of the respiratory parameter trend in predicting the patient WHF risk. The weight factors may also be determined using patient population data.

The optional therapy circuit 240 may deliver a therapy to the patient in response to the WHF risk satisfying a condition, such as exceeding the risk threshold. In an example, the system 200 may include a detector circuit configured to detect a WHF event, such as a heart failure decompensation event, using the WHF risk indicator. In an example, the detector may select one or more physiologic signals or signal metrics based on the WHF risk indicator, and use the selected signals or signal metrics to detect a WHF event. In another example, the detector may generate a composite index using a combination of physiologic signals or signal metrics each weighted by respective weight factors. The weight factors may be determined based on the WHF risk indicator. The therapy circuit 240 may deliver a therapy in response to the detection of WHF event. Examples of the therapy may include electrostimulation therapy delivered to the heart, a nerve tissue, other target tissue, a cardioversion therapy, a defibrillation therapy, or drug therapy. In some examples, the therapy circuit 240 may modify an existing therapy, such as adjust a stimulation parameter or drug dosage.

Although the discussion herein focuses on WHF risk, this is meant only by way of example but not limitation. Systems, devices, and methods discussed in this document may also be suitable for detecting various sorts of diseases or for assessing risk of developing other worsened conditions, such as cardiac arrhythmias, heart failure decompensation, pulmonary edema, pulmonary condition exacerbation, asthma and pneumonia, myocardial infarction, dilated cardiomyopathy, ischemic cardiomyopathy, valvular disease, renal disease, chronic obstructive pulmonary disease, peripheral vascular disease, cerebrovascular disease, hepatic disease, diabetes, anemia, or depression, among others.

Figure 3:
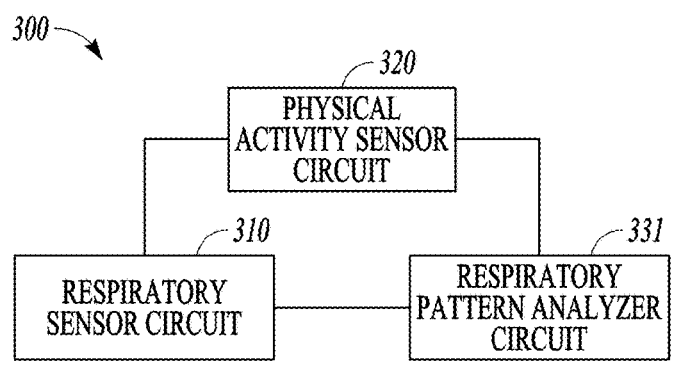
FIG. 3 illustrates generally an example of a physical activity-triggered respiratory pattern analyzer system.

FIG. 3 illustrates generally an example of a physical activity-triggered respiratory pattern analyzer system 300. The system 300 may be an embodiment of portions of the heart failure monitor system 200 for respiratory pattern analysis. The system 300 includes a respiratory pattern analyzer circuit 331, which is an embodiment of the respiratory pattern analyzer circuit 231 of the system 200, coupled to a respiratory sensor circuit 310 and a physical activity sensor circuit 320.

The physical activity sensor circuit 320 may be coupled to a physical activity sensor configured to detect patient physical activity. The physical activity sensor may be an implantable, wearable, holdable, or otherwise ambulatory sensor for sensing an intensity of physical activity or a posture state of the subject. The physical activity sensor may include a single-axis or a multi-axis accelerometer configured to sense an acceleration signal of at least a portion of the subject's body. The strength of the acceleration signal can be indicative of the physical activity level. In another example, the activity sensor can include a respiratory sensor configured to measure respiratory parameters correlative or indicative of respiratory exchange, i.e., oxygen uptake and carbon dioxide output. In an example, posture can be represented by, for example, a tilt angle sensed by a tilt switch. In another example, patient posture or physical activity information can be derived from thoracic impedance information. In healthy subjects, physical activity and posture may each follow a circadian rhythm. For instance, physical activity intensity is typically higher during the day and reduces at night, and a standing or upright posture usually occurs during the day and a lying posture occurs at night. This circadian rhythm of physical activity or posture, however, may become less pronounced or otherwise change several hours to several days before the onset of a disease state, such as a worsening heart failure. Monitoring the circadian rhythm of physical activity or posture in such instances provides a tool to predict, monitor, or treat an occurrence of impending heart failure.

The respiratory sensor circuit 310, which is an embodiment of the respiratory sensor circuit 210, may be coupled to the physical activity sensor circuit 320 to sense a respiratory signal when the detected patient physical activity satisfies a specific condition, such as when the measured acceleration is within a specific acceleration range. In some examples, the respiratory sensor circuit 310 and the physical activity sensor circuit 320 may be coupled to the same sensor, such an accelerometer sensor, configured to sense a chest motion signal. The respiratory sensor circuit 310 may process the sensed chest motion signal, such as by filtering the signal through a signal filter, to obtain a respiratory signal. The physical activity sensor circuit 320 may process the same sensed chest motion signal, such as by filtering the signal through a different signal filter, to obtain information about patient physical activity. The respiratory pattern analyzer circuit 331 may measure a respiratory metric from the physical activity-triggered respiratory signal, and generate one or more indicators of respiratory pattern variability (e.g., RSBI variability indicator) using the respiratory metrics. In some examples, the respiratory pattern analyzer circuit 331 may associate the respiratory metrics with various patient physical activity levels indicating intensity, duration, or pattern of patient physical activities, and generate one or more respiratory pattern variability indicators using the physical activity-indicated respiratory metrics. For example, the respiratory pattern analyzer circuit 331 may generate a physical activity-indicated RSBI variability indicator using daily representative RSBI measurements corresponding to specified physical activity levels. In an example, daily representative RSBI measurements corresponding to a relatively higher physical activity level (e.g., greater than 17 mG, or greater than 25 mG) may be used for generating the RSBI variability indicator. The heart failure risk analyzer circuit 234 may generate the WHF risk indicator using the physical activity-indicated RSBI variability indicator.

Figure 4:
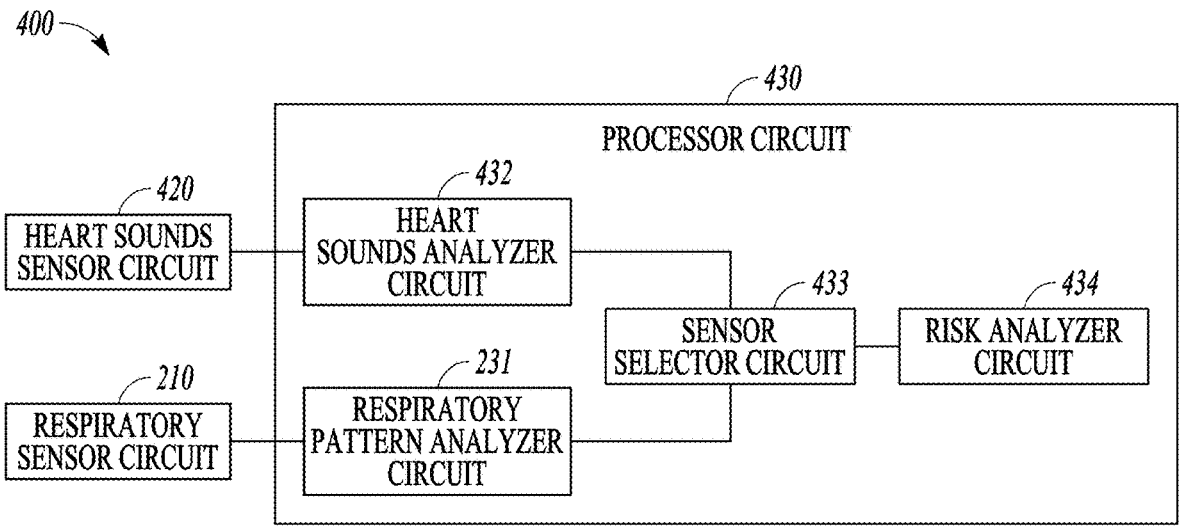
FIG. 4 illustrates generally another example of a heart failure monitor system 400 configured to assess a risk of WHF.

FIG. 4 illustrates generally another example of a heart failure monitor system 400 configured to assess patient WHF risk. The heart failure management system 400, which is an embodiment of the system 100 or the heart failure monitor system 200, may generate a WHF risk based on patient heart sounds (HS) and respiratory pattern variabilities.

The system 400 may include a respiratory sensor circuit 210, a heart sounds sensor circuit 420, and a processor 430. The heart sounds (HS) sensor circuit 420 may be coupled to a HS sensor to sense a HS signal. The HS sensor may take the form of an accelerometer, an acoustic sensor, a microphone, a piezo-based sensor, or other vibrational or acoustic sensors. The accelerometer can be a two-axis or a three-axis accelerometer. Examples of the accelerometer may include flexible piezoelectric crystal (e.g., quartz) accelerometer or capacitive accelerometer, fabricated using micro electromechanical systems (MEMS) technology. The HS sensor may be included in the AMD 110, or disposed on a lead such as a part of the lead system 108. In an example, the accelerometer may sense an epicardial or endocardial acceleration (EA) signal from a portion of a heart, such as on an endocardial or epicardial surface of one of a left ventricle, a right ventricle, a left atrium, or a right atrium. The EA signal may contain components corresponding to various HS components. In some examples, the HS sensor circuit 420 and the respiratory sensor circuit 210 may be coupled to the same sensor, such an accelerometer sensor, configured to sense a chest motion signal. The respiratory sensor circuit 210 may process the sensed chest motion signal, such as by filtering the signal through a signal filter, to obtain a respiratory signal. The HS sensor circuit 420 may process the same sensed chest motion signal, such as by filtering the signal through a different signal filter, to obtain a HS signal. In some examples, the HS sensor circuit 420 may receive patient HS signal from a storage device that stores HS signals collected from the patient The processor circuit 430, which is an embodiment of the processor circuit 230, may include a HS analyzer circuit 432, a respiratory pattern analyzer circuit 231, a sensor selector circuit 433, and a risk analyzer circuit 434. The HS analyzer circuit 432 may analyze the HS signal and determine the signal quality, such as a signal-to-noise ratio (SNR), of the HS signal. In an example, the HS analyzer circuit 432 may detect one or more HS components including a first (S1) heart sound, a second (S2) heart sound, a third (S3) heart sound, or a fourth (S4) heart sound. One or more HS metrics may be generated using the detected HS components including, for example, an intensity (e.g., amplitude or signal energy under the curve) of one of the HS component, or one or more HS-based cardiac timing intervals, such as a pre-ejection period (PEP) such as measured between the onset of the QRS to the S1 heart sound, a systolic timing interval (STI) such as measured between the onset of the QRS complex on the ECG to the S2 heart sound, a left-ventricular ejection time (LVET) such as measured as an interval between S1 and S2 heart sounds, or a diastolic timing interval (DTI) such as measured between the S2 heart sound and the onset of the subsequent QRS complex on the ECG, among others. Among other HS metrics, intensities of S3 or S4, and HS-based cardiac timing intervals may be correlated with cardiac contractility or cardiac diastolic function, and may be predictive of patient heart failure status. The HS analyzer circuit 432 may generate quality indicator of one or more HS metrics, such as an SNR of S3 intensity, or an SNR of PEP measurement.

The respiratory sensor circuit 210 may sense a respiratory signal, and the respiratory pattern analyzer circuit 231 may measure one or more respiratory metrics, as previously discussed with reference to FIG. 2, The sensor selector circuit 433 may select between the HS metrics such as produced by the HS analyzer circuit 432, and the respiratory pattern variability such as produced by the respiratory pattern analyzer circuit 231. The selection may be based on the HS quality such as produced by the HS analyzer circuit 432. In an example, the HS metrics may be selected if the HS quality satisfies a signal quality condition (e.g., a SNR exceeding a threshold SNR). In another example, the respiratory pattern metrics, such as RSBI variability, may be selected if the HS quality fails to satisfy the signal quality condition (e.g., a SNR falling below the threshold SNR).

The risk analyzer circuit 434, which is an embodiment of the risk analyzer circuit 234, may determine the patient WHF risk indicator using the selected signal metrics. In an example, the sensor selector circuit 433 may assign different weight factors to the HS metrics and the respiratory metrics based on at least the HS quality. If the HS quality satisfies the signal quality condition indicating a high HS quality (such as exceeding a specific threshold or falling within a specific range), a larger weight factor may be assigned to the HS metrics and a smaller weight factor may be assigned to the respiratory metrics. Conversely, if a low HS quality is indicated, a smaller weight factor may be assigned to the HS metrics and a larger weight factor may be assigned to the respiratory metrics. The risk analyzer circuit 434 may determine the patient WHF risk indicator using a combination of the respiratory metrics (including the respiratory pattern variability such as RSBI variability indicator) and the HS metrics each weighted by their respective weight factors.

Figure 5:
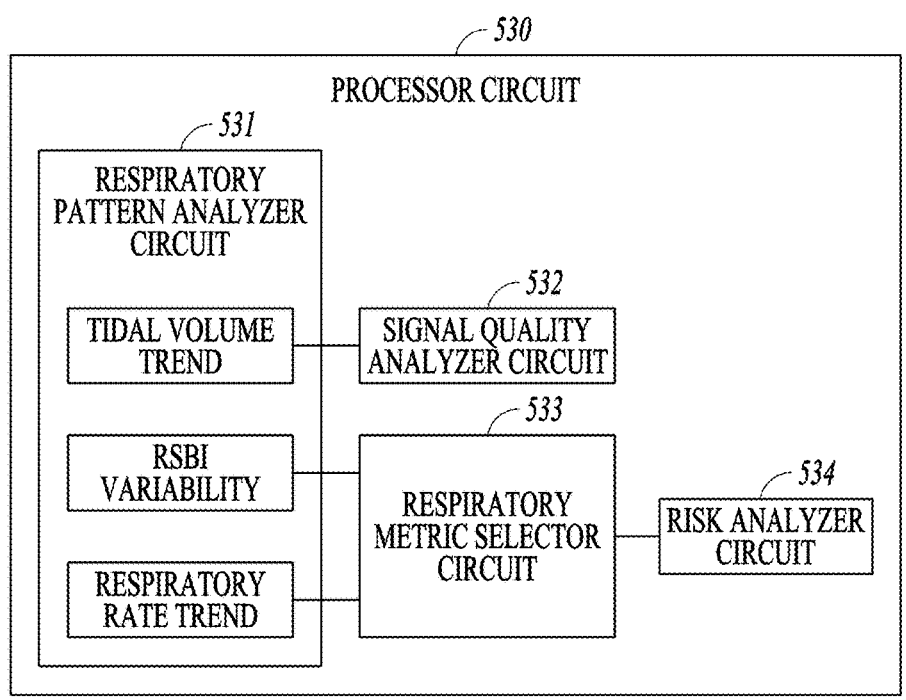
FIG. 5 illustrates generally an example of a processor circuit for assessing patient WHF risk using respiratory metrics.

FIG. 5 illustrates generally an example of a processor circuit 530 for assessing patient WHF risk using respiratory metrics. The processor circuit 530 is an embodiment of the processor circuit 230, and includes a respiratory pattern analyzer circuit 531, a signal quality analyzer circuit 532, a respiratory metric selector circuit 533, and a risk analyzer circuit 534. The respiratory pattern analyzer circuit 531, which is an embodiment of the respiratory pattern analyzer circuit 231, may generate a plurality of respiratory metrics including a tidal volume trend (TVT), an RSBI variability, and a respiratory rate trend (RRT). The signal quality analyzer circuit 532 is coupled to the respiratory pattern analyzer circuit 531 to generate a TVT quality indicator. In an example, the TVT quality indicator may be represented by a signal-to-noise ratio of the TVT.

The respiratory metric selector circuit 533 may selected one of more respiratory metrics from those generated by the respiratory pattern analyzer circuit 531 based on the TVT quality indicator. In an example, the selection is made between the RSBI variability indicator and the RRT. As the RSBI represents a ratio of respiratory rate to tidal volume, a low-quality TVT such as due to noisy tidal volume measurement may affect the reliability of RSBI measurement. Thus, the RSBI may be more reliably used for predicting patient WHF risk if TVT has a high signal quality. The RSBI variability indicator may be selected if the TVT quality satisfies a specific signal quality condition (e.g., a SNR exceeding a threshold SNR). In another example, the RRT may be selected if the TVT quality fails to satisfy the specific signal quality condition. The risk analyzer circuit 534, which is an embodiment of the risk analyzer circuit 234, may determine the WHF risk indicator using the selected signal metrics.

In some examples, the respiratory metric selector circuit 533 may assign different weight factors to the respiratory metrics (e.g., RSBI variability, the RRT, among other respiratory metrics) based on at least the TVT quality. If the TVT quality satisfies the signal quality condition indicating a high TVT quality, a larger weight factor may be assigned to the RSBI variability indicator and a smaller weight factor may be assigned to the RRT. Conversely, if a low TVT quality is indicated, a smaller weight factor may be assigned to the RSBI variability indicator and a larger weight factor may be assigned to the RRT. The risk analyzer circuit 534 may determine the patient WHF risk indicator using a combination of the RSBI variability and the RRT, optionally along with other respiratory metrics, each weighted by their respective weight factors.

Figure 6A:
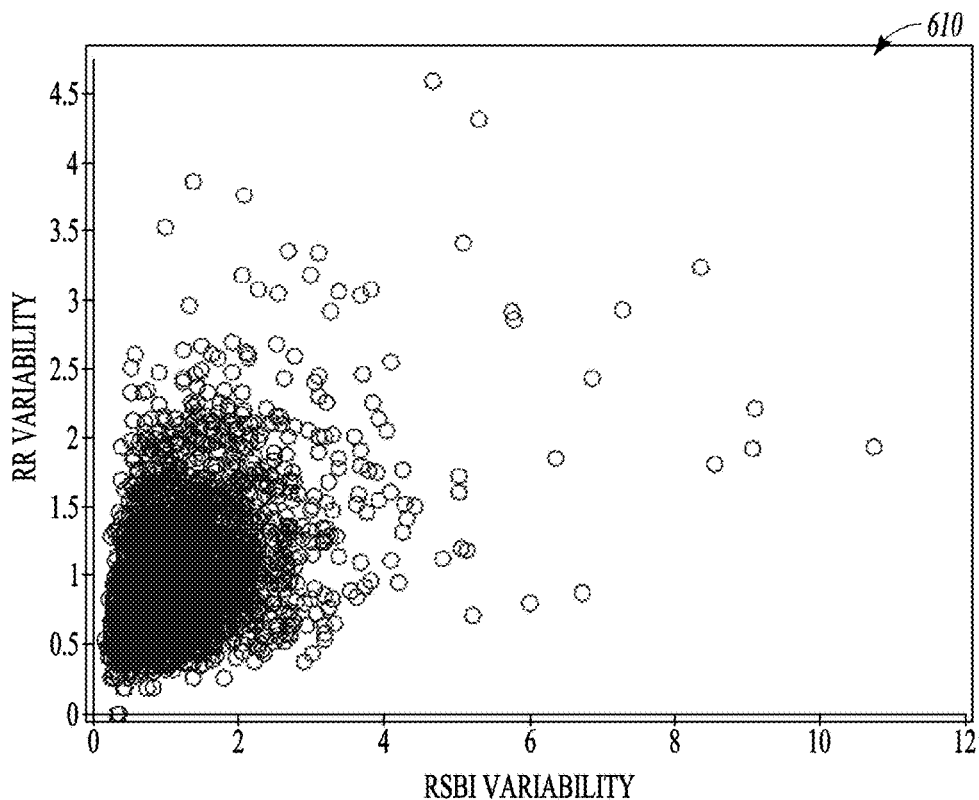
FIGS. 6A-6B illustrate rapid-shallow breathing index and respiratory rate trend for WHF risk stratification either being used individually or in combination.
Figure 6B:
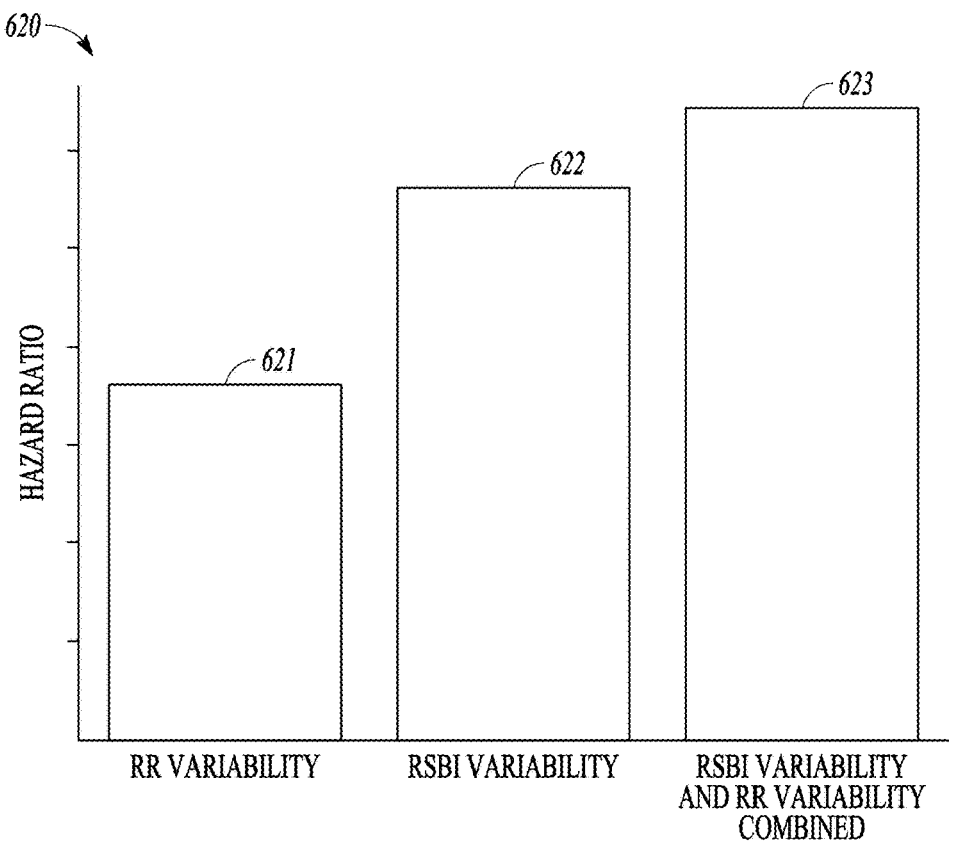

FIGS. 6A-6B are graphs illustrating, by way of example, two respiratory metrics, RSBI and respiratory rate trend (RRT), for WHF risk stratification either being used individually or in combination. Graph 610 in FIG. 6A illustrates a scatter plot of respiratory rate (RR) variability measurements (on y-axis) and RSBI variability measurements (on x-axis). The data points are collected from multiple patients. Each data point represents substantially concurrent measurements of RR variability and RSBI variability from the same subject. In this example, the RR variability and the RSBI variability are computed using standard deviation of measurements of the respective metrics over multiple days. Graph 610 shows a weak correlation between RSBI variability and RR variability. This may suggest that RSBI variability offers additional WHF risk stratification power complementary to that of the RR variability. Graph 620 in FIG. 6B illustrates a hazard ratio 621 of RR variability alone, a hazard ratio 622 of RSBI variability alone, and a hazard ratio 623 of composite metrics with RR variability and the RSBI variability combined. A hazard ratio as illustrated in 620 measures how often a substantially high respiratory metric (e.g., RR variability, RSBI variability, or RR variability and RSBI variability as combined exceeding their respective threshold or satisfying specific condition) happens in a first group of patients with WHF events compared to how often the substantially high respiratory metric happens in a second group of patients without WHF events over time. A hazard ratio of one means that there is no difference between the first and second groups. A higher hazard ratio of greater than one means a higher predicative power of WHF events associated with the signal metric. In the example of FIG. 6B, the hazard ratio 622 of RSBI variability alone is greater than the hazard ratio 621 of RR variability alone, and the hazard ratio 623 of the composite metrics with RR variability and the RSBI variability combined is greater than the hazard ratio 622 of RSBI variability alone. This may suggest that, in this example, the RSBI variability has a higher predictive power of WHF risk than the RR variability, and a combination of RSBI variability and the RR variability may further improve the WHF risk stratification power. In an example, the HF risk analyzer circuit 234, or the risk analyzer circuit 434 or 534, may use both the composite metrics with RSBI variability and the RR variability combined to determine the WHF risk indicator.

Figure 7:
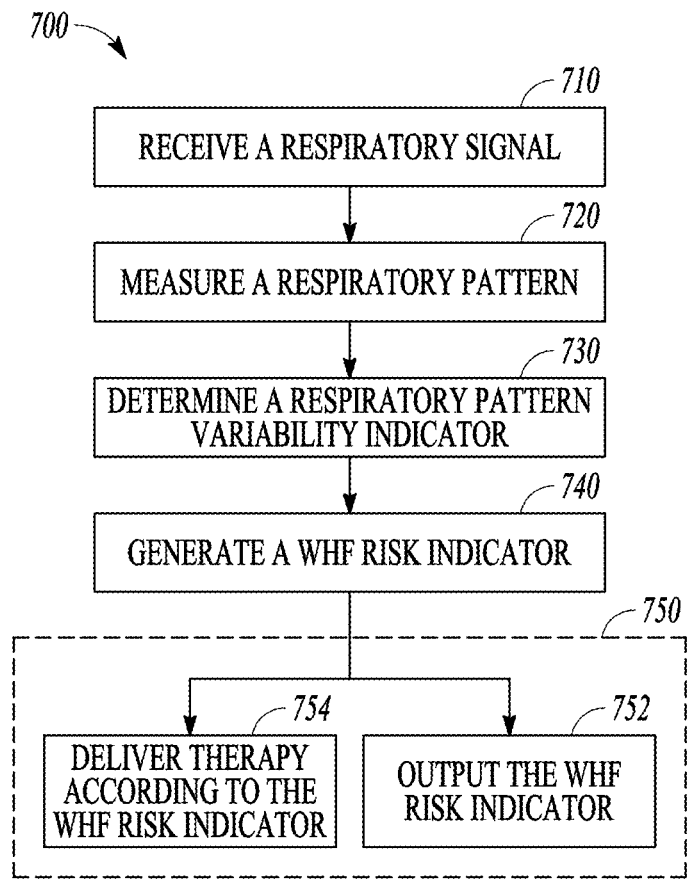
FIG. 7 illustrates generally an example of a method for assessing a patient risk for a future WHF event.

FIG. 7 illustrates generally an example of a method 700 for assessing a patient risk for a future WHF event. The method 700 may be implemented and executed in an ambulatory medical device (AMD), such as an implantable or wearable medical device, or in a remote patient management system. In various examples, the method 700 may be implemented in and executed by the AMD 110, one or more devices in the external system 125, or the heart failure monitor system 200 or a modification thereof.

The method 700 commences at step 710, where a respiratory signal may be received. In an example, the respiratory signal may be sensed using the respiratory sensor circuit 210 that is coupled to one or more physiologic sensors, as previously discussed with reference to FIG. 2. The sensors may be implantable, wearable, holdable, or other ambulatory respiratory sensors. The sensed respiratory signal may include a respiration waveform that represents the change in airflow or lung volume during a respiratory cycle. Alternatively, the sensed physiologic signal, such as a thoracic impedance signal or a cardiac electrical activity signal, may be filtered using one or more signal filters to obtain the respiratory signal. In some examples, the respiratory signal sensed from a patient may be stored in a storage device, such as an electronic medical record system. The respiratory signal may be retrieved from the storage device in response to a user input or triggered by a specific event.

At 720, a respiratory pattern may be measured from the respiratory signal. One or more respiratory metrics may be generated from the respiratory signal. Examples of the respiratory metrics may include a respiratory rate, a tidal volume, a minute ventilation, a respiratory sound, or a respiratory pattern, among other respiratory metrics. The respiratory pattern may include a rapid-shallow breathing index (RSBI) computed as a ratio of a respiratory rate measurement to a tidal volume measurement. Other examples of respiratory pattern may include Cheyne-Stokes pattern, cluster breathing, Kussmaul's breathing, apneustic breathing, or ataxic breathing.

At 730, one or more of the respiratory metrics may each be trended over time, and a respiratory pattern variability indicator may be determined using the one or more respiratory metric trends. The variability of may be represented by a standard deviation, a variance, a range (e.g., a difference between minimum and maximum, an interquartile range between upper and lower quartiles, a difference between $10^{th}$ to $90^{th}$ percentiles or other ranges), or other measures of spreadness of the respiratory metric. An example of the respiratory pattern variability indicator is an RSBI variability. The RSBI variability may be computed using measurements of daily representative RSBI over multiple days. Examples of daily representative RSBI may include a daily minimum RSBI, a daily maximum RSBI, a daily median RSBI, a daily mean RSBI, or a specific percentile of multiple RSBI measurements during a day ($RSBI_{X\%}$). In an example, the representative RSBI is a lower percentile (e.g., <50%) of daily RSBI measurements. A lower percentile RSBI represents rapid-shallow breathing pattern at elevated physical activities. Heart failure patients are more likely to demonstrate shortness of breath when they are active. As such, a lower percentile RSBI may be a better predictor to patient heart failure status than a higher percentile (e.g., >50%) RSBI.

In various examples, the respiratory signal may be sensed at 710 when the patient undergoes a specific level of physical activity. One or more respiratory metrics, including respiratory patterns, may be measured at 720 from the respiratory signal, and one or more respiratory pattern variability indicators (e.g., RSBI variability indicator) may be determined at 730 using the respiratory metrics associated with various patient physical activity levels indicating intensity, duration, or pattern of patient physical activities.

At 740, a WHF risk indicator may be generated using at least the respiratory pattern variability indicator. The respiratory pattern variability indicator, such as the RSBI variability, may be compared to one more threshold values or value ranges to classify the patient WHF risk into one of risk categories. In an example, the WHF risk indicator may be generated using two or more respiratory metric trends, such as selected from a respiratory rate trend, a respiratory rate variability, an RSBI trend, an RSBI variability, a tidal volume trend, or a tidal volume variability, among others. In another example, the WHF risk indicator may be generated using higher-order statistics of the respiratory metrics. The heart failure risk analyzer circuit 234 may determine the WHF IF risk indicator using a pre-determined mapping between a WHF risk indicator and a plurality of respiratory parameter trends. The mapping may be represented by a look-up table or an association map. Alternatively, the WHF risk indicator may be generated using a weighted combination of the respiratory variability indicators, optionally in addition to other respiratory metrics.

In various examples, the WHF risk indicator may be generated further using heart sound signals. One or more HS components (e.g., S1, S2, S3, or S4) may be detected from the HS signal, and one or more HS metrics may be generated based on the detected HS components. By way of example and not limitation, the HS metrics may include an intensity of one of the HS component, or one or more HS-based cardiac timing intervals. The WHF risk indicator may be generated using either the HS metrics, or the respiratory metrics including the respiratory pattern variability such as RSBI variability indicator, depending on a quality measure of a HS signal metric. An example of the signal quality measure may include a signal-to-noise ratio (SNR). In an example, the HS metrics may be selected for generating the WHF risk indicator if the HS quality satisfies a signal quality condition (e.g., a SNR exceeding a threshold SNR), or the respiratory pattern metrics such as RSBI variability may be selected if the HS quality fails to satisfy the signal quality condition. Alternatively, in some example, the WHF risk indicator may be generated using a combination of the respiratory metrics (including the respiratory pattern variability such as RSBI variability indicator) and the HS metrics each weighted by their respective weight factors. Weight factors assigned to the HS metrics and weight factors assigned to the respiratory metrics may be based on the HS metric quality. In an example, if the HS quality satisfies the signal quality condition indicating a high HS quality, a larger weight factor may be assigned to the HS metrics and a smaller weight factor may be assigned to the respiratory metrics. Conversely, if a low HS quality is indicated, a smaller weight factor may be assigned to the HS metrics and a larger weight factor may be assigned to the respiratory metrics.

In various examples, the WHF risk indicator may be generated using a plurality of respiratory metrics, including a tidal volume trend (TVT), an RSBI variability, and a respiratory rate trend (RRT). One or more respiratory metrics may be selected based on a quality indicator of the TVT, such as a signal-to-noise ratio (SNR) of the TVT. In an example, the selection is made between the RSBI variability indicator and the RRT. The RSBI variability indicator may be selected if the TVT quality satisfies a signal quality condition (e.g., a SNR exceeding a threshold SNR), and the RRT may be selected if the TVT quality fails to satisfy the signal quality condition (e.g., a SNR falling below the threshold SNR).

In some examples, the patient WHF risk indicator may be generated using a combination of the RSBI variability and the RRT, optionally along with other respiratory metrics, each weighted by their respective weight factors. The weight factors assigned to various respiratory metrics (such as RSBI variability, the RRT, among other respiratory metrics) may be based on the TVT quality. In an example, if the TNT quality satisfies the signal quality condition indicating a high TVT quality, a larger weight factor may be assigned to the RSBI variability and a smaller weight factor may be assigned to the RRT. Conversely, if a low TVT quality is indicated, a smaller weight factor may be assigned to the RSBI variability and a larger weight factor may be assigned to the RRT.

At 750, the WHF risk indicator may be output to a user or a process. At 752, a human-perceptible presentation of the WHF risk indicator may be generated, and displayed on a display screen of the user interface 220. The information may be presented in a table, a chart, a diagram, or any other types of textual, tabular, or graphical presentation formats. Hard copies of signals and information related to the generation of WHF risk indicator may be printed. In an example, alerts, alarms, emergency calls, or other forms of warnings may be generated to warn the system user about patient WHF risk or a detection of a WHF event. The WHF detection or the WHF risk may be output to a process such as an instance of a computer program executable in a microprocessor. Additionally or alternatively, at 754, the detected WHF risk may trigger a therapy delivered to the patient, such as using the therapy circuit 240. The therapy may be delivered to the patient in response to the WHF risk satisfying a condition, such as exceeding the risk threshold. Examples of the therapy may include electrostimulation therapy delivered to the heart, a nerve tissue, other target tissue, a cardioversion therapy, a defibrillation therapy, or drug therapy. In some examples, an existing therapy may be modified, such as by adjusting a stimulation parameter or drug dosage.

The method 700 may additionally include a step of detecting a WHF event, such as a heart failure decompensation event, using the WHF risk indicator. In an example, one or more physiologic signals or signal metrics may be selected based on the WHF risk indicator. A composite detection index may be generated using the WHF risk-indicated signals or signal metrics. A WHF event is detected if the composite detection index satisfies a specific detection condition, such as exceeding a detection threshold. In an example, the composite detection index may be determined using a combination of physiologic signals or signal metrics each weighted by respective weight factors. The weight factors may be determined based on the WHF risk indicator. A therapy may be delivered to the patient in response to the detection of WHF event.

Figure 8:
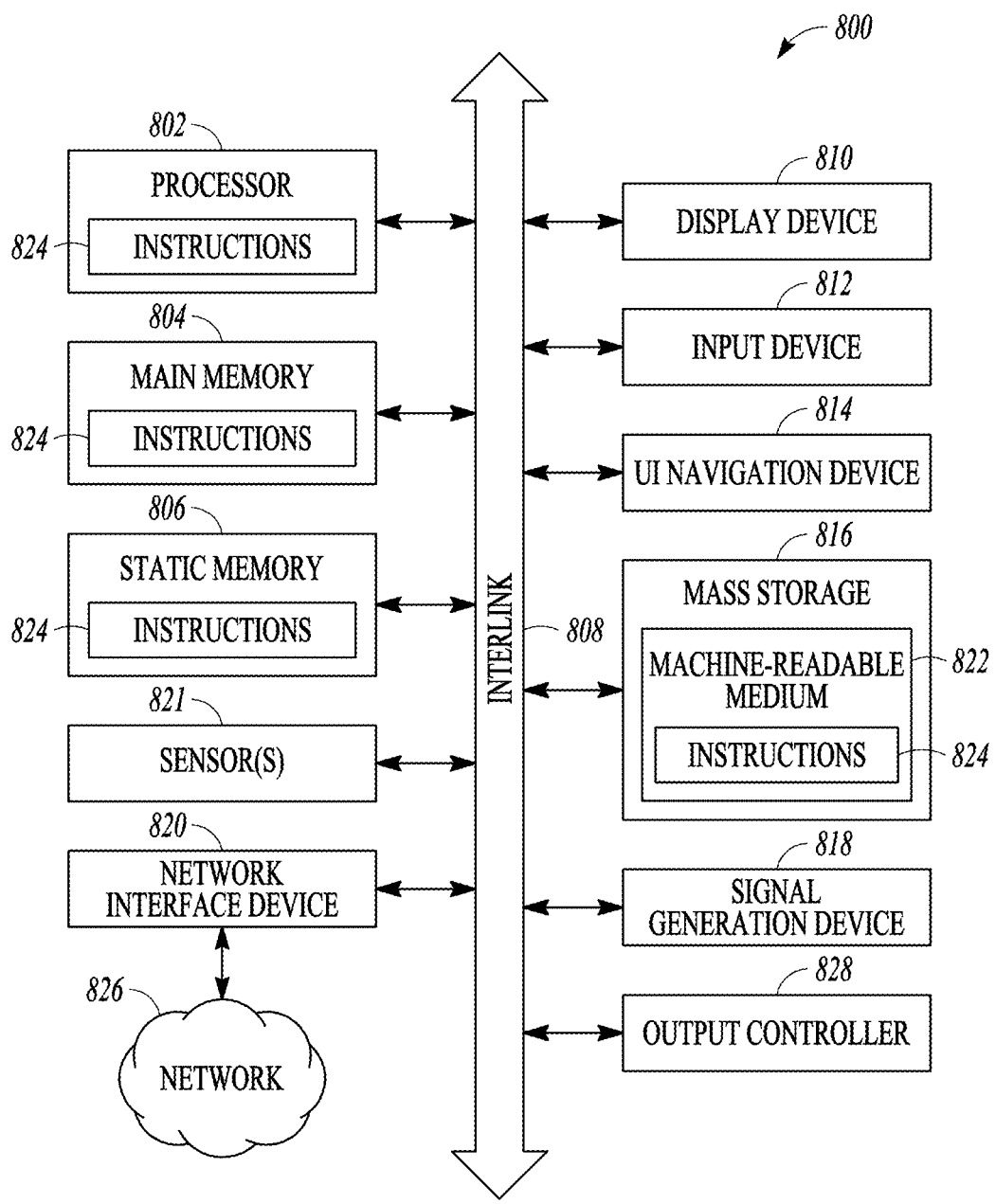
FIG. 8 illustrates generally a block diagram of an example machine upon which any one or more of the techniques discussed herein may perform.

FIG. 8 illustrates generally a block diagram of an example machine 800 upon which any one or more of the techniques (e.g., methodologies) discussed herein may perform. Portions of this description may apply to the computing framework of various portions of the LCP device, the IMD, or the external programmer.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specific operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensors. The machine 800 may include an output controller 828, such as a serial (e.g., universal serial bus (USB), parallel, or other wired or wireless (e.g., infrared (IR), near field communication (NFC), etc. connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine-readable media.

While the machine-readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for assessing a patient risk for a future worsening heart failure (WHF) event, comprising:
   a signal receiver circuit configured to receive a respiratory signal from the patient;
   a processor circuit, including:
      a respiratory pattern analyzer circuit configured to measure a rapid-shallow breathing index (RSBI) parameter using the received respiratory signal, and to determine an RSBI variability indicator indicative of temporal variation of the measured RSBI parameter; and
      a risk analyzer circuit configured to generate a WHF risk indicator using the determined RSBI variability indicator.

2. The system of claim 1, comprising a sensor circuit coupled to an impedance sensor configured to sense a thoracic impedance correlated to respiration,
   wherein the respiratory patter analyzer circuit is configured to detect a respiratory rate and a tidal volume using the sensed thoracic impedance, and to generate the RSBI based on a ratio of the detected respiratory rate to the detected tidal volume.

3. The system of claim 1, wherein the RSBI parameter includes a daily representative RSBI, and
   wherein the respiratory pattern analyzer circuit is configured to determine the RSBI variability indicator using measurements of daily representative RSBI over multiple days.

4. The system of claim 3, wherein the daily representative RSBI includes a daily minimum RSBI.

5. The system of claim 3, wherein the daily representative RSBI includes a specific percentile of measurements of daily RSBI parameters, the specific percentile being lower than 50-th percentile.

6. The system of claim 1, comprising an activity detection circuit configured to detect patient physical activity, wherein the signal receiver circuit configured to receive a respiratory signal when the detected patient physical activity satisfies a specific condition.

7. The system of claim 1, wherein:
   the signal receiver circuit is further configured to receive a heart sounds signal;
   the processor circuit includes a heart sound analyzer circuit configured to generate a heart sound metric using the received heart sounds signal; and
   the risk analyzer circuit is configured to:
   generate the WHF risk indicator using the RSBI variability indicator if the received heart sounds signal fails to satisfy a signal quality condition; and
   generate the WHF risk indicator using the heart sound metric if the received heart sounds signal satisfies the signal quality condition.

8. The system of claim 1, wherein:
   the respiratory pattern analyzer circuit is further configured to generate, from the sensed respiratory signal, one or more respiratory metrics including a respiratory rate trend, a respiratory rate variability over time, a tidal volume trend, or a tidal volume variability over time; and
   the risk analyzer circuit is configured to generate the WHF risk indicator further using the generated one or more respiratory metrics.

9. The system of claim 8, wherein the respiratory pattern analyzer circuit is configured to generate a tidal volume trend and a respiratory rate trend from the sensed respiratory signal, and the risk analyzer circuit is configured to:
   generate the WHF risk indicator using the RSBI variability indicator if the tidal volume trend satisfies a quality condition; and generate the WHF risk indicator using the respiratory rate trend if the tidal volume trend fails to satisfy the quality condition.

10. The system of claim 1, comprising a detector circuit configured to detect a WHF event based on the generated WHF risk indicator.

11. The system of claim 1, comprising a therapy circuit configured to generate a heart failure therapy when the WHF risk indicator satisfies a specific condition.

12. The system of claim 1, wherein the respiratory pattern analyzer circuit is configured to determine the RSBI variability indicator using a range between two percentiles of measurements of RSBI parameters over one or more days.

13. A method for assessing a patient risk for a future worsening heart failure (WHF) event using a medical system, the method comprising:
   receiving a respiratory signal from the patient via a signal receiver circuit;
   measuring, via a respiratory pattern analyzer circuit, a rapid-shallow breathing index (RSBI) parameter from the received respiratory signal;
   determining an RSBI variability indicator indicative of temporal variation of the measured RSBI parameter; and
   generating a WHF risk indicator using the determined RSBI variability indicator via a risk analyzer circuit.

14. The method of claim 13, wherein the RSBI parameter includes a daily representative RSBI, and
   wherein the RSBI variability indicator is determined using measurements of daily representative RSBI over multiple days.

15. The method of claim 14, further comprising determining a baseline RSBI using the measurements of daily representative RSBI over multiple days, wherein generating the WHF risk indicator is further based on the baseline RSBI.

16. The method of claim 13, further comprising generating a heart sound metric using a heart sounds signal, wherein generating the WHF risk indicator includes:
   generating the WHF risk indicator using the RSBI variability indicator if the received heart sounds signal satisfies a signal quality condition; and
   generating the WHF risk indicator using the heart sound metric if the received heart sounds signal fails to satisfy the signal quality condition.

17. The method of claim 13, further comprising generating one or more respiratory metrics from the sensed respiratory signal, the one or more respiratory metrics including a respiratory rate trend, a respiratory rate variability over time, a tidal volume trend, or a tidal volume variability over time, wherein generating the WHF risk indicator is further based on the one or more respiratory metrics.

18. The method of claim 17, wherein the one or more respiratory metrics include a tidal volume trend and a respiratory rate trend from the sensed respiratory signal, wherein generating the WHF risk indicator includes:
   generating the WHF risk indicator using the RSBI variability indicator if the tidal volume trend satisfies a quality condition; and
   generating the WHF risk indicator using the respiratory rate trend if the tidal volume trend fails to satisfy the quality condition.

19. The method of claim 13, further comprising delivering a heart failure therapy when the WHF risk indicator satisfies a specific condition.

20. The method of claim 13, wherein the RSBI variability indicator includes a range between two percentiles of measurements of RSBI parameters over one or more days.

* * * * *